(12) United States Patent
Nachum

(10) Patent No.: US 6,393,326 B1
(45) Date of Patent: May 21, 2002

(54) BEDSORE TREATMENT USING ELECTRICAL IMPULSES

(75) Inventor: Zvi Nachum, Tiberias (IL)

(73) Assignee: Lifecare Ltd., Tiberias (IL)

(*) Notice: Subject to any disclaimer, the term of this patent is extended or adjusted under 35 U.S.C. 154(b) by 31 days.

(21) Appl. No.: 09/584,488

(22) Filed: Jun. 1, 2000

(51) Int. Cl.⁷ ................................................ A61N 1/18
(52) U.S. Cl. .......................... 607/50; 607/68; 607/74
(58) Field of Search ............................. 607/50, 68, 70, 607/72–74, 62; 128/898

(56) References Cited

U.S. PATENT DOCUMENTS

| 1,480,353 A | 1/1924 | Wappler |
| 1,890,270 A | 12/1932 | Takoaka |
| 3,872,859 A | 3/1975 | Pitzen et al. |
| 4,117,846 A | 10/1978 | Williams |
| 4,727,878 A | * 3/1988 | Levine |
| 4,738,250 A | * 4/1988 | Fulkerson et al. |
| 5,158,081 A | * 10/1992 | McWhorter et al. |
| 5,484,387 A | 1/1996 | Pitzen |

\* cited by examiner

Primary Examiner—Jeffrey R. Jastrzab
(74) Attorney, Agent, or Firm—Mark M. Friedman

(57) ABSTRACT

A non-invasive method for the treatment of sores having substantially zero electrical activity, including the steps of: (a) situating a pair of spaced-apart electrodes in contact with healthy tissue on opposite sides of an area containing cells to be treated, and (b) externally inducing a percutaneous flow of electrical current between said electrodes through said area by establishing an external bipolar voltage wave form across said electrodes at a frequency of between 2 Hz and 10 Hz. Preferably, at least one of the positive and negative voltage half cycles contains at least two peaks. The treatment method is particularly appropriate for bedsores.

13 Claims, 3 Drawing Sheets

BEDSORE TREATMENT USING ELECTRICAL IMPULSES

FIELD AND BACKGROUND OF THE INVENTION

The present invention relates to a system and method for promoting the healing of damaged animal tissue, including human tissue by propagation of an electric current flow through the tissue. In particular, the invention relates to a method for promoting the healing of bedsores and the like by propagation of an electric current flow through the damaged tissue.

U.S. Pat. No. 4,117,846 to Williams discloses a disposable skin conducting electrode assembly and electrode therefor for use on a patient. The electrode assembly comprises an electrolyte pad, an electrode and an adhesive pad.

It is taught in the above-mentioned patent that such an electrode can be used for various kinds of electrical treatments, including electrosurgery, medical diathermy (thermopenetration), and pain relief using transcutaneous nerve stimulation, aiding the setting and proper healing of broken bones and fractured vertebrae, and improving the curvature of the spine.

An electrode of this type can also be used for the transmission of an electrical impulse for directly stimulating a nerve or nerve pathway for restoring the physiological functions of a damaged nerve system. U.S. Pat. No. 4,117,846 teaches that an electrode assembly of this kind can be used to apply an electrical current for enhancing or promoting the healing of traumatized, injured or displaced tissue. The healing of bedsores or decubitis ulcers, surgical incisions, skin ulcerations, and lacerations is aided by long term application of high frequency current, and in some cases, by the application of low voltage DC current.

In contrast to U.S. Pat. No. 4,117,846, which mentions the application of high frequency current, U.S. Pat. No. 4,738,250 to Fulkerson, et al., discloses a medical electrical apparatus impressing a low frequency, bipolar, voltage wave form through spaced-apart electrodes, across a damaged area of living animal tissue to cause a low, bipolar, current to flow through the damaged area to increase the metabolic activity of viable cells in that area and hence to accelerate healing. The current flow is monitored and used to control the magnitude of the voltage wave to cause the magnitude of current flow to be within the desired parameters. The frequency, wave form and voltage of the impressed voltage-wave and the current flow are all below a level which can damage typical living cells.

According to U.S. Pat. No. 4,738,250, the above-described increase in metabolic activity results in at least the following positive benefits: accelerated production of adenosine triphosphate (ATP), increased synthesis of cell protein, improved cell membrane transport system, and accelerated production of collagen.

U.S. Pat. No. 4,738,250 further discloses that this electrical treatment signal reduces the concentration of free radicals that appear when cells are damaged. These free radicals are known to cause further damage by cell membrane disruption; and this reduction, done in accordance with the teachings of the invention, tends to reduce or eliminate this continuing damage without the current flow itself damaging the cells or otherwise insulting the living tissue being treated.

The electrical treatment signal disclosed by U.S. Pat. No. 4,738,250 is characterized by a current within a range of about 20 to 900 microamperes, resulting in the voltage of the treatment signal to be within a range of from zero to 30 volts. It is further disclosed that currents between 20 and 600 microamperes give good results, and that optimal results are obtained between 500 and 600 microamperes. Current flows approaching 1000 microamperes or 1 milliampere have proved destructive to cells in the pathway of such flow.

U.S. Pat. No. 4,738,250 also teaches a treatment signal having a treatment signal frequency within a range of about 0.1 to 15 Hz. However, in contrast to this relatively wide frequency range of 0.1 Hz to 15 Hz, U.S. Pat. No. 4,738,250 further discloses that the frequency of the wave form used can be varied from a very low frequency to a frequency slightly less than 1 Hz. Good results were obtained between 0.1 Hz and 0.9 Hz, and optimal results were obtained using a frequency of 0.5 Hz.

The form of the wave form applied is bipolar. In a first embodiment of the invention, the voltage of the treatment signal is increased in a linear fashion during each treatment signal time period until the current of the treatment signal attains its preselected value; and in a second embodiment of the invention, the voltage is increased nonlinearly, in an exponential fashion, during each treatment signal time period until the current attains its preselected value.

To the best of our knowledge, however, the treatment systems and methods described above have not been implemented in the treatment of bedsores. It may be stated with certainty that these prior art systems and methods are not common practice. It must be emphasized that there are no known, effective treatments for curing bedsores. According to T. McNamara, an expert in the prevention of amputation, treatment consists of wound management (keeping the affected area clean, administering antibiotics) combined with interventive procedures to improve the flow of blood, such as balloon angioplasty or bypass surgery (Dr. Thomas McNamara, "Non-Surgical Techniques to Heal Foot Ulcers, Prevent Amputation and Relieve Leg Pain", WebMD, 1999). Thus, the fact that the above-described systems and methods (applying electrical wave forms) have not been implemented is a clear indication of their ineffectiveness in the treatment of bedsores.

There is therefore a recognized need for, and it would be highly advantageous to have, an effective method for promoting the healing of bedsores and the like. Moreover, it would be of particular advantage to have amethod that can provide simple and inexpensive treatment by the propagation of an electric current flow through the damaged tissue. Finally, it would be highly advantageous to have a method that is mild and non-invasive, in view of the generally frail condition of those afflicted by bedsores.

SUMMARY OF THE INVENTION

According to the teachings of the present invention there is provided a method for the treatment of sores including the steps of: (a) situating a pair of spaced-apart electrodes in contact with healthy tissue on opposite sides of an area containing cells to be treated, and (b) externally inducing a percutaneous flow of electrical current between the electrodes through the area by establishing an external bipolar voltage wave form across the electrodes at a frequency of between 2 Hz and 10 Hz, wherein the sores are sores having substantially zero electrical activity.

According to further features in preferred embodiments of the invention described below, the frequency of the external bipolar voltage wave form across the electrodes is between 2 Hz and 5 Hz.

According to still further features in the described preferred embodiments, the external bipolar voltage wave form includes a positive voltage half cycle and a negative voltage half cycle, wherein at least one of the positive voltage half cycle and negative voltage half cycle contains at least two peaks.

In another aspect of the present invention there is provided a method for the treatment of sores including the steps of: (a) situating a pair of spaced-apart electrodes in contact with healthy tissue on opposite sides of an area containing cells to be treated, and (b) externally inducing a percutaneous flow of electrical current between the electrodes through the area by establishing a substantially cyclic voltage wave form across the electrodes, wherein the substantially cyclic voltage wave form includes a positive voltage half cycle and a negative voltage half cycle, and wherein at least one of the positive voltage half cycle and negative voltage half cycle contains at least two peaks, wherein the sores are sores having substantially zero electrical activity.

According to still further features in the described preferred embodiments, the sores having substantially zero electrical activity are bedsores.

According to still further features in the described preferred embodiments, the frequency of the external bipolar voltage wave form across the electrodes is between 16 Hz and 30 Hz.

Other aspects of the inventive treatment procedures are described more fully in my co-pending U.S. patent application, Ser. No. 09/593,399 filed Jun. 14, 2000, whose content is fully incorporated by reference for every purpose as if fully set forth herein.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
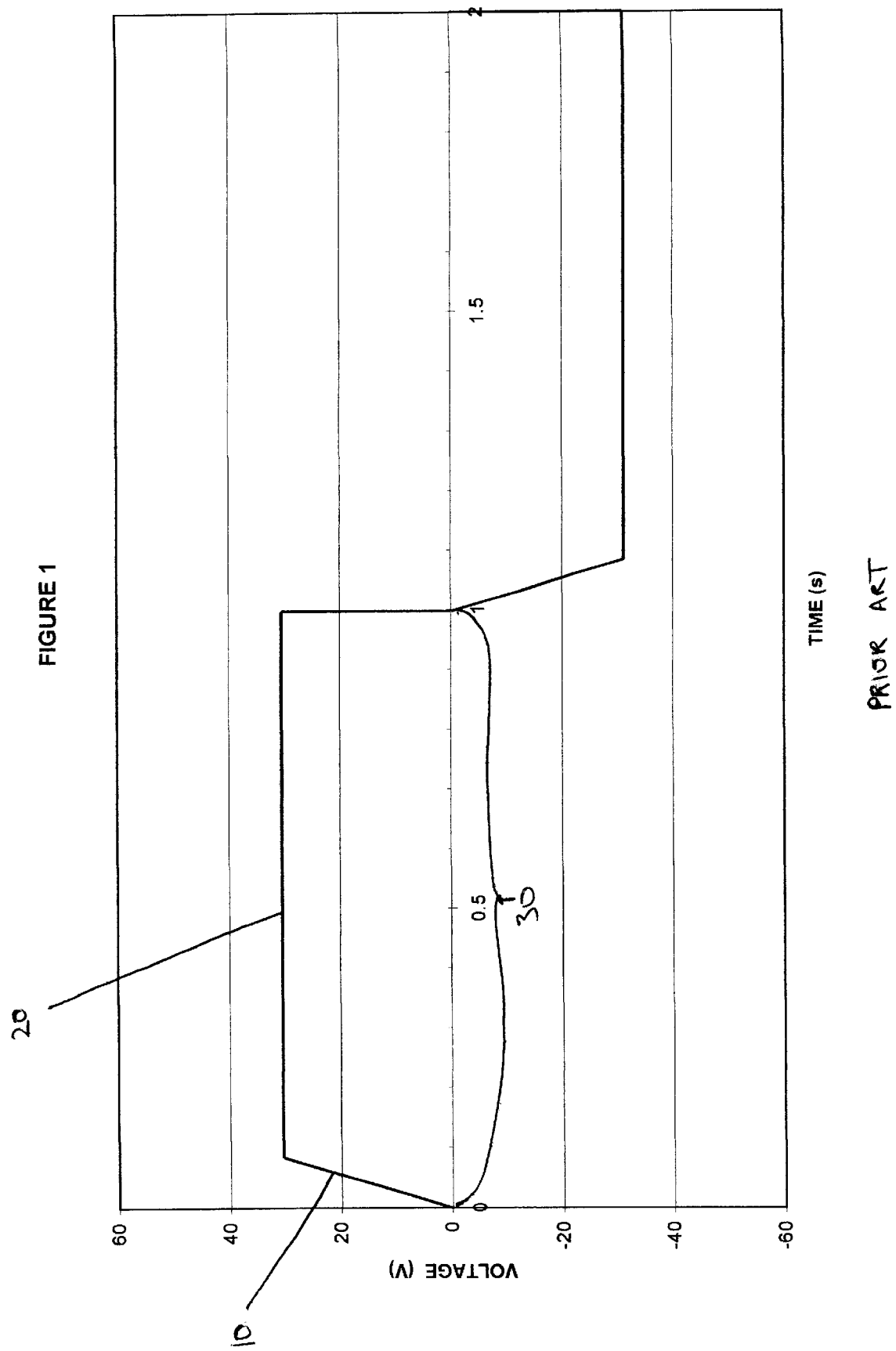
FIG. 1 is a graph illustrating an electrical wave form according to an optimal embodiment of the prior art.

The principles and operation of a method and procedure for promoting the healing of bedsores by propagation of an electric current flow through the damaged tissue, according to the present invention, may be better understood with reference to the drawings and the accompanying description.

Without wishing to be limited, the treatment mechanism is based on a discovery of how the body treats sores and maladies of various kinds. The brain sends electric signals through the nervous system to the various parts of the body. Special signals of a particular form and frequency are transmitted to areas identified as having damaged tissues. Although the frequency, shape, and intensity of the signals may vary from individual to individual, and from malady to malady, there is a very strong common denominator between them.

The information-gathering parts of the nervous system provide a tremendous amount of data, continually updated, about the condition of the body and its surroundings. The sense organs give a detailed picture of the outside world, but there are also many sensors within the body that monitor the activity and condition of the body. Some of these sensors, known as proprioreceptors, are found in muscles, joints, ligaments, and tendons. Proprioreceptors in the muscles, for example, inform the central nervous system about how much a muscle has contracted, and also register pain.

Other specialized sensors monitor the blood circulation, respiration and digestion. Baroreceptors measure blood pressure in the great arteries of the body, and chemoreceptors analyze the levels of oxygen and carbon dioxide in the blood. The lungs and airway contain stretch receptors, and the activity of the heart is monitored by specialized receptors in the atria and ventricles.

The sensors send messages to the central nervous system in the form of tiny electrical impulses. Each sensor is attached to a long fiber called a dendrite, which is a long extension of a nerve cell, or "axon". Each single nerve contains thousands of dendrites, which are collected together in bundles to make up a single nerve, and the whole complex structure leads from the sensors to the spinal cord.

A cross-section of the spinal cord reveals a gray area in the middle, surrounded by white matter. The gray matter consists of nerve cells and their connections, and the white matter contains nerve fibers, many of which are arranged in tracts leading to specific locations in the brain. Information gathered by the various sensors of the body passes into the gray matter in the spinal cord, where it is organized according to type and then relayed through the above-mentioned nerve fiber tracts to the command centers of the central nervous system in the brain.

When a particular area of tissue has been damaged, the brain recognizes the "distress signals" conveyed from the local sensors, and supervises and directs the healing effort accordingly. The supervisory role of the brain includes a continual transmission of "instructions" as electrical impulses that are sent to the affected area and, if necessary, to other organs and parts of the body as well. These may include instructions to increase the blood supply to the affected area. It has been established by the inventor that bedsores behave in a completely different fashion than other types of sores, ulcers, and the like. In bedsores, the tissue, including nerve cells, is dead, such that all electrical activity has been completely interrupted. Because it is highly probable that the contact with the brain has been lost or greatly impaired, the healing effort is severely hampered, and consequently, the healing effort is performed in a more local, less organized fashion.

Moreover, communication via the central nervous system is not lost only in the area of the bedsore. Often, the communication break in the relatively small area of the bedsore triggers a gradual cessation of communication or electrical activity with other nervous pathways belonging to the same "relay station" of the nervous system. In some cases, particularly with the elderly and with people with weakened body defenses, a local bedsore can spread to the point that entire limbs need amputating.

The electrical waves of the present invention essentially mimic the waves that are normally produced by the brain and transmitted by the brain to damaged tissues. Because there is no electrical activity whatsoever coming from the brain, the present invention provides to the damaged area electrical signals that are substantially identical from an operational standpoint to those transmitted by the brain through the nervous system. The body "recognizes" the signal and provides the appropriate healing response. Eventually, vestiges of vitality return to the damaged area, and the electrical activity of the area is sustained without further external electrical stimulation. With communication restored along the nervous system pathway, the brain can again transmit electrical signals to the affected area, which indicates that the body is fundamentally capable of furthering the healing process on its own.

Before explaining at least one embodiment of the invention in detail, it is to be understood that the invention is not limited in its application to the details of construction and the arrangement of the components set forth in the following description or illustrated in the drawing. The invention is capable of other embodiments or of being practiced or carried out in various ways. Also, it is to be understood that the phraseology and terminology employed herein is for the purpose of description and should not be regarded as limiting.

Referring now to the drawings, FIG. 1 is a graph of a voltage wave form according to the prior art, in which voltage (volts) is plotted versus time (seconds). U.S. Pat. No. 4,738,250 to Fulkerson et al. discloses a so-called "square wave" form wherein the voltage rises in a linear fashion 10 until a predetermined current flow is reached and then is maintained 20 until the end of a treatment signal time period which is the half cycle determined by the selected frequency. Thus, a frequency of 0.5 Hz corresponds to a cycle of 2 seconds, or a half cycle 30 of 1 second.

U.S. Pat. No. 4,738,250 also discloses a similar wave form, termed "modified square waves", wherein the voltage increases as an exponential function until the predetermined current flow reaches the predetermined level, and wherein the voltage is held at that level until the end of that half treatment signal time period.

The above-mentioned patent also teaches a treatment signal having a treatment signal frequency to be within a range of about 0.1 to 15 Hz. However, in contrast this relatively wide frequency range of 0.1 Hz to 15 Hz, the above-mentioned patent discloses that the frequency of the wave form used can be varied from a very low frequency to a frequency slightly less than 1 Hz. Good results were reported for frequencies between 0.1 Hz and 0.9 Hz, with optimal results being obtained at a frequency of 0.5 Hz.

Against the background of the prior art, it was surprising to discover that the most effective frequencies according to the present invention lie in the range of 2–30 Hz, and most preferably in the range of 2–5 Hz.

These and further differences between the electrical waves of the present invention and those of the prior art are more fully appreciated when viewed in the context of the healing process in the body. Because the electrical waves of the present invention are very similar to the waves that are normally transmitted by the brain to damaged tissues, the body "recognizes" the signal and provides the appropriate healing response and support. Without wishing to be limited by the above theory, it has been discovered that the above-mentioned electrical stimulation frequency range (2–30 Hz, and most preferably 2–5 Hz) is of critical importance in improving the healing process and in reviving the healing efforts of the body.

For the same reason, the shape of the electrical wave is of great importance. The straight or smooth wave forms disclosed by U.S. Pat. No. 4,738,250 do not resemble the waves that are normally produced by the brain and transmitted via the central nervous system, hence their effectiveness is extremely limited, despite the propagation of an electric field in the affected area.

Figure 2:
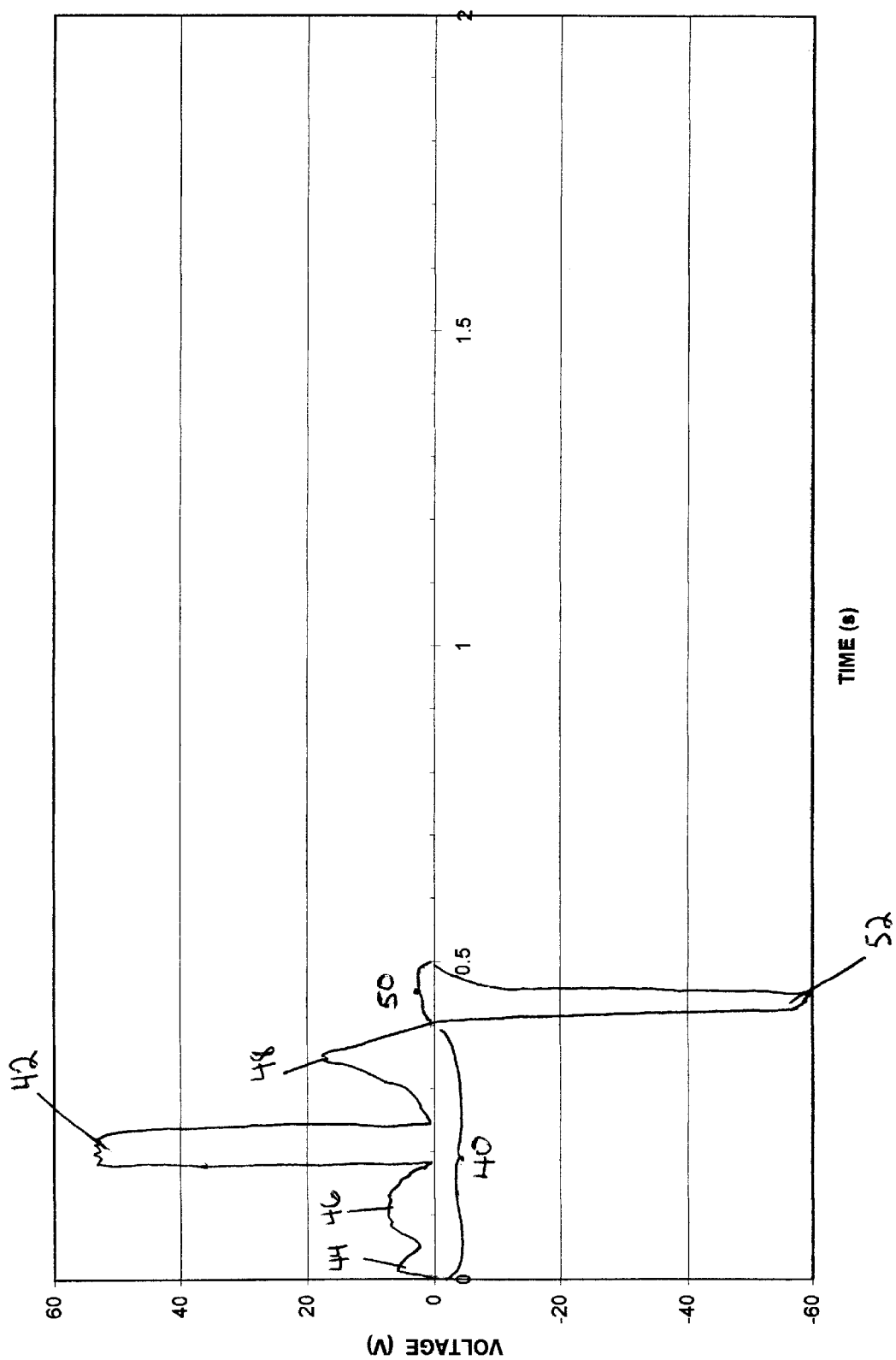
FIG. 2 is a graph illustrating an electrical wave form according to the present invention.

A typical wave form which, according to the present invention, is propagated to areas containing bedsores and the like, is provided in FIG. 2. The cycle time is 0.5 seconds, corresponding to a frequency of 2 Hz. The wave form is bipolar, with one major peak 42 in the positive half cycle 40 and one major peak 52 in the negative half cycle 50. The major peaks have an absolute voltage of 50–60 Volts. The actual voltage delivered to the affected area of the body is considerably lower, however, due to the impedance of the skin. Several smaller peaks 44,46,48 with voltages ranging from 5–20 Volts appear in the positive half cycle 40. It should also be noted that the duration of the positive half cycle 40 and the duration of the negative half cycle 50 are not equal. The positive half cycle 40 lasts for about 0.4 seconds, while the negative half cycle 50 lasts for only about 0.1 seconds.

Thus, the wave form according to the present invention is not necessarily symmetric in terms of the peak shapes, peak intensities, and the duration of the positive and negative half cycles. Moreover, these characteristics may also change somewhat from cycle to cycle. These minor changes are an attempt to reflect wave forms that typically transmitted through the central nervous system to damaged tissues in the body. Without wishing to be limited, it is believed that such minor changes in the wave form actually promote healing, because the body "recognizes" the signal as coming from the central nervous system and hence responds faster and with a higher level of activity.

Figure 3:
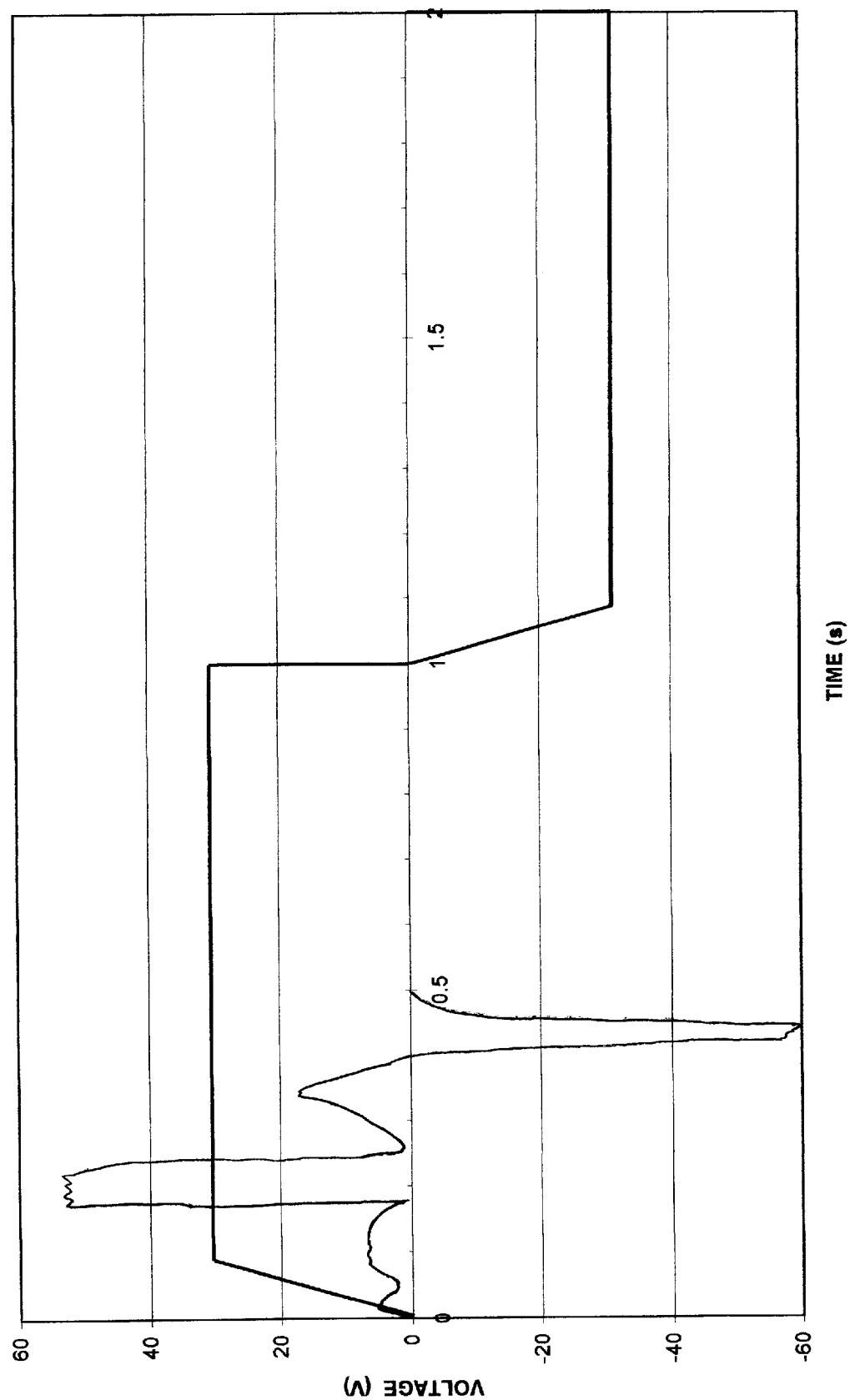
FIG. 3 is a graph in which the above-mentioned wave forms are compared.

FIG. 3 is a graph in which the typical wave form of the present invention, provided in FIG. 2, is compared with the optimal wave form according to the prior art, provided in FIG. 1. The width of the individual peaks in the wave form of the present invention are about 1/10 of the peak width in the wave form of the prior art. Other differences in the wave form have been described above.

Thus, according to the present invention there is provided a method for the treatment of sores having substantially zero electrical activity including the steps of: (a) situating a pair of spaced-apart electrodes in contact with healthy tissue on opposite sides of an area containing cells to be treated; and (b) externally inducing a percutaneous flow of electrical current between the electrodes through the area by establishing a substantially cyclic voltage wave form across the electrodes, wherein the substantially cyclic voltage wave form includes a positive voltage half cycle and a negative voltage half cycle, and wherein at least one of the positive voltage half cycle and negative voltage half cycle contains at least two peaks. Preferably, each full cycle contains 3–10 peaks.

As used herein in the specification and in the claims section that follows, the term "sores having substantially zero electrical activity" refers to a type of sore that does not sustain independent electrical activity (i.e., without external and/or foreign stimulation). A common example of a sore having substantially zero electrical activity is bedsores.

In the medical literature, the term "bedsore" refers to an area of skin damage, and often ulceration, that is highly correlated with a restriction of the blood supply to the affected area. The immediate cause of the blood restriction is usually constant pressure on the affected areas. As used herein in the specification and in the claims section that follows, the term "bedsore" refers to, but is not limited to, the above-described skin damage and ulcerations.

As used herein in the specification and in the claims section that follows, the term "peak" refers to a portion of a voltage half cycle having an absolute maximum voltage followed by a slope in the direction of the zero voltage line.

As used herein in the specification and in the claims section that follows, the term "substantially cyclic voltage wave form" refers to a wave form, consisting of various peaks, which repeats itself. Although the wave form need not be identical from cycle to cycle, and small changes in the wave form may even be preferable, the general appearance of the wave form is repetitive.

Reference is now made to the following example, which together with the above description, illustrates the invention in a non-limiting fashion.

EXAMPLE 1

Upon discovering that a bedsore is absolutely devoid of electrical activity, the above-described clinical procedure was tested on a patient suffering from bedsores. The initial reading of electrical activity in and around the bedsore was zero, i.e., below the sensitivity of the measuring instrument. The affected area was electrically stimulated by externally inducing a percutaneous flow of electrical current between two electrodes through the damaged area. The voltage waves were of the form of the wave according to one embodiment of the present invention, illustrated in FIG. 2. The duration of the electrical stimulation was 20 minutes.

It was discovered by the inventor that the electrical fields in and around the damaged area continued to maintain electrical activity, on the order of microvolts, after ceasing the external electrical stimulation. These electrical fields were very similar to typical electrical fields of sores that heal readily without external intervention. With time, however, the magnitude of the electrical field decayed, such that after about 1.5 hours, the electrical activity dropped back to zero.

At this point, an additional 20 minute treatment was initiated, the additional treatment being substantially identical to the first electrical treatment. Upon ceasing the external electrical stimulation, the independent electrical activity was monitored once again. As before, the damaged area continued to display electrical activity, on the order of microvolts, this time lasting for over 2.5 hours before decaying to zero activity.

With each successive treatment using electrical stimulation, the independent electrical activity of the damaged area lengthened, and after the eleventh of such treatments, the electrical activity was permanently sustained.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention

What is claimed is:

1. A method for the treatment of a sores the method including the steps of:
    (a) situating a pair of spaced-apart electrodes in contact with healthy tissue on opposite sides of the sore; and
    (b) externally inducing a percutaneous flow of electrical current between said electrodes through said area by establishing a substantially cyclic voltage wave form across said electrodes, wherein said substantially cyclic voltage wave form includes a positive voltage half cycle and a negative voltage half cycle, and wherein at least one of said positive voltage half cycle and negative voltage half cycle contains at least two peaks,
    said cyclic voltage wave form having a frequency in a range of 2 Hz to 30 Hz,
    and wherein the sore has substantially zero electrical activity.

2. The treatment method of claim 1, wherein said frequency of said cyclic voltage wave form across said electrodes is between 2 Hz and 10 Hz.

3. The treatment method of claim 1, wherein said frequency of said cyclic voltage wave form across said electrodes is between 2 Hz and 5 Hz.

4. The treatment method of claim 1, wherein said frequency of said cyclic voltage wave form across said electrodes is between 16 Hz and 30 Hz.

5. A method for the treatment of a sore, the method including the steps of:
    (a) situating a pair of spaced-apart electrodes in contact with healthy tissue on opposite sides of the sore; and
    (b) externally inducing a percutaneous flow of electrical current between said electrodes through said area by establishing an external bipolar voltage wave form across said electrodes,
    wherein said bipolar voltage wave form substantially mimics a bipolar voltage wave form produced by a human body.

6. The treatment method of claim 5, wherein the sore has substantially zero electrical activity.

7. The treatment method of claim 5 or claim 6, wherein said frequency of said external bipolar voltage wave form across said electrodes is between 2 Hz and 30 Hz.

8. The treatment method of claim 5 or claim 6, wherein said frequency of said external bipolar voltage wave form across said electrodes is between 2 Hz and 10 Hz.

9. The treatment method of claim 5 and claim 6, wherein said frequency of said external bipolar voltage wave form across said electrodes is between 2 Hz and 5 Hz.

10. A method for the treatment of a sore, the method including the steps of:

(a) situating a pair of spaced-apart electrodes in contact with healthy tissue on opposite sides of the sore; and (b) externally inducing a percutaneous flow of electrical current between said electrodes through said area by establishing an external bipolar voltage wave form across said electrodes, wherein said bipolar voltage wave form is characterized by a voltage that substantially continuously varies with time, and wherein the sore has substantially zero electrical activity.

11. The treatment method of claim 10, wherein said frequency of said cyclic voltage wave form across said electrodes is between 2 Hz and 30 Hz.

12. The treatment method of claim 10, wherein said frequency of said cyclic voltage wave form across said electrodes is between 2 Hz and 10 Hz.

13. The treatment method of claim 10, wherein said frequency of said cyclic voltage wave form across said electrodes is between 2 Hz and 5 Hz.

* * * * *